United States Patent [19]

O'Malley et al.

[11] Patent Number: 5,091,541
[45] Date of Patent: Feb. 25, 1992

[54] HEXAHYDROPYRROLO(2,3-B)INDOLE CARBAMATES, UREAS, AMIDES AND RELATED COMPOUNDS

[75] Inventors: Gerard J. O'Malley, Newtown, Pa.; Richard C. Allen, Flemington, N.J.; John I. White, Harleysville, Pa.

[73] Assignee: Hoechst-Roussel Pharmaceuticals Inc., Somerville, N.J.

[21] Appl. No.: 602,559

[22] Filed: Oct. 24, 1990

Related U.S. Application Data

[62] Division of Ser. No. 480,706, Feb. 1, 1990, Pat. No. 4,983,616.

[51] Int. Cl.$^5$ .......................................... C07D 487/00
[52] U.S. Cl. ................................... 548/429; 546/270; 548/406
[58] Field of Search ................. 548/429, 406; 546/270

[56] References Cited

PUBLICATIONS

March, Advanced Organic Chemistry, 3rd Edition, pp. 338–341; 364–365; 577; 802–83; 310–313 (1985).

*Primary Examiner*—Cecilia Shen
*Attorney, Agent, or Firm*—Barbara V. Maurer; Tatsuya Ikeda

[57] ABSTRACT

There are disclosed various compounds of the formula below,

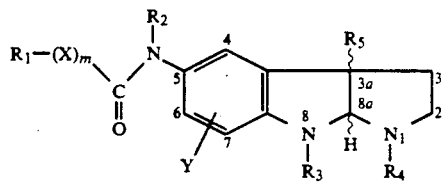

where
X is O, S, NH, N-loweralkyl, or N-arylloweralkyl;
Y is hydrogen, fluorine, chlorine, bromine, nitro, loweralkyl, loweralkoxy, or triloweralkylsilyl;
$R_1$ is loweralkyl, halogen-substituted loweralkyl, aryl, arylloweralkyl, cycloalkyl, heteroaryl or heteroarylloweralkyl;
$R_2$ is hydrogen, loweralkyl or arylloweralkyl;
$R_3$ is loweralkyl or arylloweralkyl;
$R_4$ is hydrogen, loweralkyl, loweralkenyl, loweralkynyl, arylloweralkyl, formyl, loweralkylcarbonyl, arylloweralkylcarbonyl or loweralkoxycarbonyl;
$R_5$ is hydrogen or loweralkyl; and
m is 0 or 1, with the proviso that when m is O, $R_1$ may also be hydrogen.

which compounds are useful for alleviating various memory dysfunctions characterized by a cholinergic deficit such as Alzheimer's disease.

4 Claims, No Drawings

HEXAHYDROPYRROLO(2,3-B)INDOLE CARBAMATES, UREAS, AMIDES AND RELATED COMPOUNDS

This is a division of a prior application Ser. No. 480,706, filed Feb. 1, 1990, now U.S. Pat. No. 4,983,616.

The present invention relates to compounds of the formula,

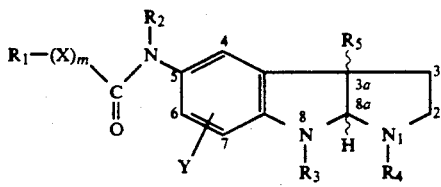

where
- X is O, S, NH, N-loweralkyl, or N-arylloweralkyl;
- Y is hydrogen, fluorine, chlorine, bromine, nitro, loweralkyl, loweralkoxy, or triloweralkylsilyl;
- $R_1$ is loweralkyl, halogen-substituted loweralkyl, aryl, arylloweralkyl, cycloalkyl, heteroaryl or heteroarylloweralkyl;
- $R_2$ is hydrogen, loweralkyl or arylloweralkyl;
- $R_3$ is loweralkyl or arylloweralkyl;
- $R_4$ is hydrogen, loweralkyl, loweralkenyl, loweralkynyl, arylloweralkyl, formyl, loweralkylcarbonyl, arylloweralkylcarbonyl or loweralkoxycarbonyl;
- $R_5$ is hydrogen or loweralkyl; and
- m is 0 or 1, with the proviso that when m is 0, $R_1$ may also be hydrogen, which compounds are useful for alleviating various memory dysfunctions characterized by a cholinergic deficit such as Alzheimer's disease.

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term loweralkenyl shall mean an alkenyl group having from 2 to 6 carbon atoms and one double bond.

The term loweralkynyl shall mean an alkynyl group having from 2 to 6 carbon atoms and one triple bond.

The term cycloalkyl shall mean a cycloalkyl group having from 3 to 7 carbon atoms in the ring. Said cycloalkyl group may be substituted with 1 or 2 loweralkyl groups.

The term halogen shall mean fluorine, chlorine, bromine or iodine.

The term halogen-substituted loweralkyl shall mean a loweralkyl group which is substituted with one or more halogen atoms.

The term aryl in each occurrence shall mean an unsubstituted phenyl group or a phenyl group substituted with 1, 2 or 3 substituent groups each of which being independently loweralkyl, halogen, nitro, loweralkoxy, hydroxy or trifluoromethyl.

The term heteroaryl in each occurrence shall mean a group depicted by the formula

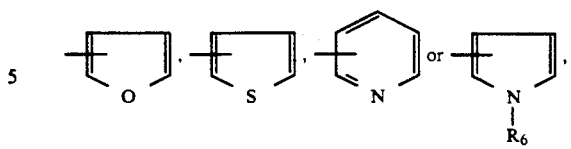

where $R_6$ is hydrogen or loweralkyl.

The compounds of this invention are prepared by utilizing the synthetic scheme described below.

In structural formulas depicting compounds involved in this invention, heavy lines (—) coming out of the 3a-carbon and 8a-carbon of the 1,2,3,3a,8,8a-hexahydropyrrolo[2,3-b]indole ring system signify that the two substituents are above the average plane of the three-ring system, whereas dotted lines (....) signify that the two substituents are below the average plane of the three-ring system, and wavy lines (~) signify that the two substituents are both either above or below said average plane. Because of conformational constraints, the two substituents at the 3a- and 8a-positions must be both above said average plane or both below said average plane. Thus, in formulas (I), (II) and (III), the substituents at the 3a- and 8a-carbons are cis inasmuch as they are on the same side of the three ring system. Where said substituents are both above the average plane of the three ring system, the configuration will be referred to as 3aS-cis and where both substituents are below the average plane of the ring, the configuration will be referred to as 3aR-cis.

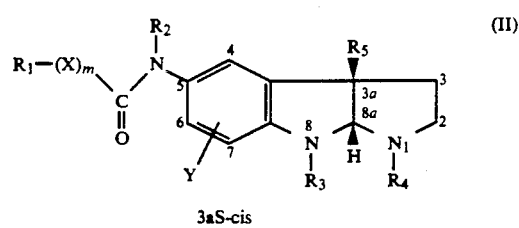

3aS-cis

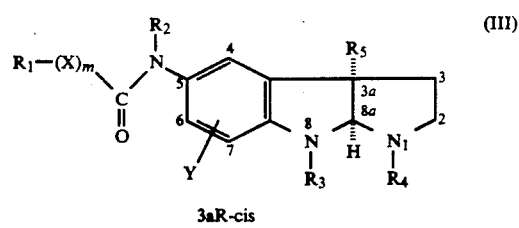

3aR-cis

Throughout the specification and the appended claims, when the inventors intend to designate in a single formula (to save space) that the compound is 3aS-cis, or 3aR-cis, or a racemic or other mixture of the two, that formula will contain wavy lines as in formula (I).

It is the intent of the present inventors to claim both of said cis isomers, namely, 3aS-cis isomer and 3aR-cis isomer for each compound name or structural formula although sometimes only one isomer is shown in the specification in order to save space. It is also the intent of the present inventors to claim all mixtures of the 3aS-cis and 3aR-cis isomers including the racemic mixture (1:1 ratio of 3aS-cis:3aR-cis).

SYNTHETIC SCHEME

In the description of synthetic steps presented below, the definitions of X, Y, m and $R_1$ through $R_6$ are as defined above unless as otherwise stated or indicated otherwise.

STEP A

Starting with a compound of formula II where Y' is hydrogen, fluorine, chlorine, bromine, loweralkyl, loweralkoxy or triloweralkylsilyl and utilizing the synthetic scheme disclosed in Julian and Pikl, J. Amer. Chem. Soc., 57,563 (1935), one can prepare a compound of formula III as outlined in the diagram presented below. For details of the synthetic scheme, the reader is referred to the original article.

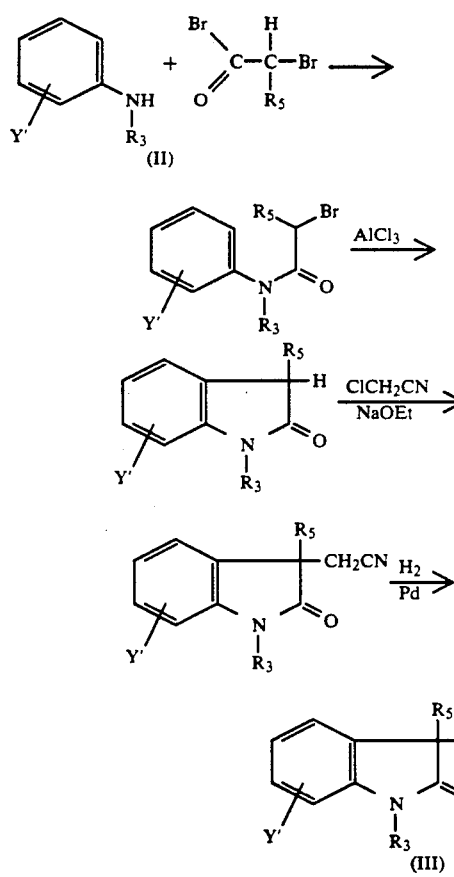

STEP B

Compound III is allowed to react with sodium metal and ethanol in substantially the same manner as described in the article by Julian and Pikl identified above to obtain a compound of Formula IV. Again, the reader is referred to the original article for details of this reaction.

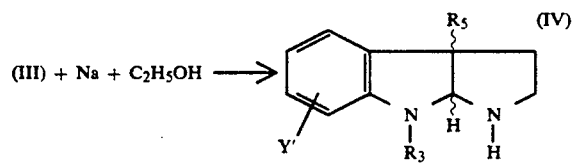

STEP C

Compound III is allowed to react with ethyl chlorformate and thereafter the product is allowed to react with LiAlH$_4$ in substantially the same manner as described in Yu and Brossi, Heterocycles, 27, 1709 (1988) to afford a compound of Formula V.

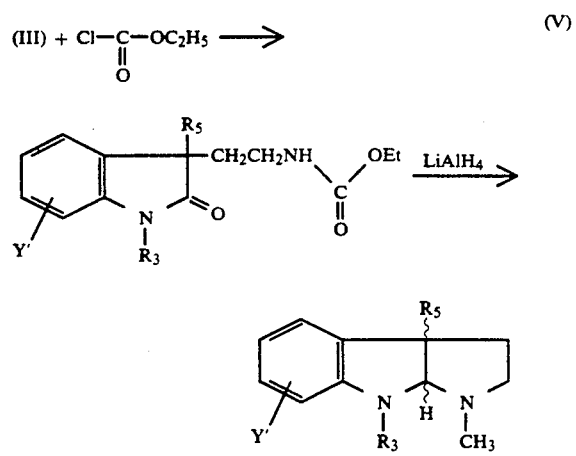

STEP D

Compound IV is allowed to react with a halide compound of the formula $R_4'$—Hal where $R_4'$ is loweralkyl, loweralkenyl, loweralkynyl or arylloweralkyl and Hal is chlorine or bromine in a routine manner known to the art to afford a compound of Formula VI.

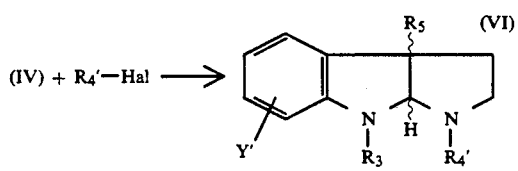

STEP E

Compound IV is allowed to react with formic-acetic mixed anhydride or with formic anhydride in a routine manner known to the art to afford a compound of Formula VII.

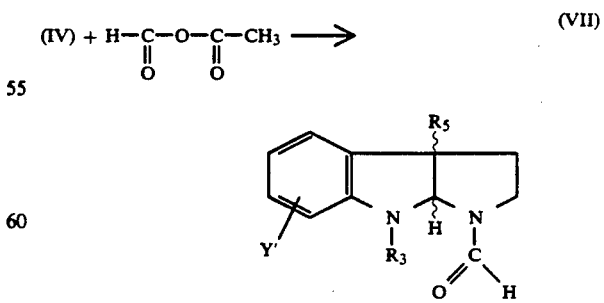

STEP F

Compound IV is allowed to react with a compound of the formula,

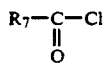

where R₇ is loweralkyl, arylloweralkyl or loweralkoxy, in a routine manner known to the art to afford a compound of Formula VIII.

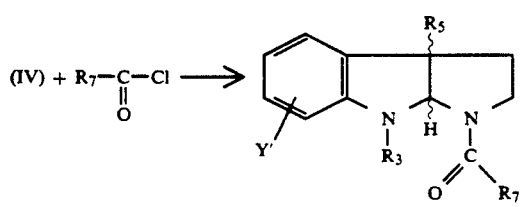

STEP G

A compound of Formula IX which is obtained from STEP B, C, D, E or F is allowed to react with nitronium tetrafluoroborate (NO₂BF₄) to afford a compound of Formula X. This reaction is typically conducted in a suitable solvent such as acetonitrile at a temperature of about −50° to 82° C. It is preferable that the molar ratio between Compound IX and NO₂BF₄ be about 1.0–1.1.

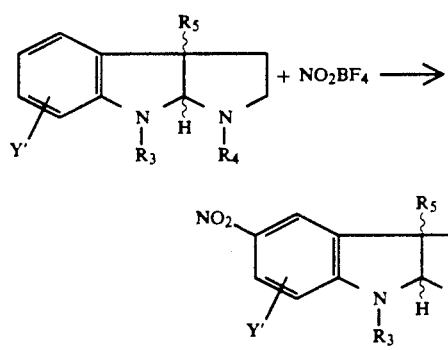

STEP H

A compound of Formula IXa which is obtained from STEP B, C, D, E or F is allowed to react with NO₂BF₄ in substantially the same manner as in STEP G, except that the molar ratio between Compound IXa and NO₂BF₄ is preferably 2.0–2.2, to afford a compound of Formula XI.

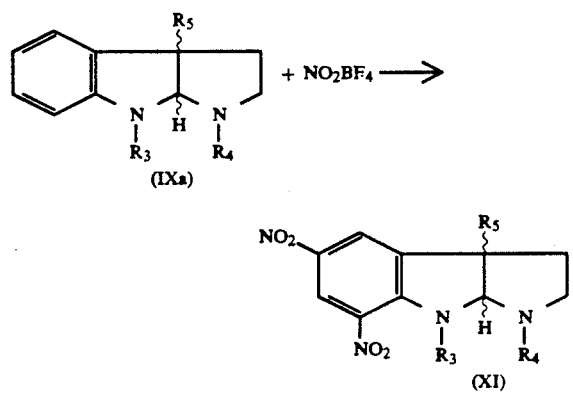

STEP I

A compound of Formula XII which is obtained from STEP G or H is hydrogenated with the aid of a platinum or palladium catalyst such as plantinum oxide or palladium on carbon to afford a compound of Formula XIII. Since compound XIII is relatively unstable, it is used for the subsequent reactions described below without isolation from the solution.

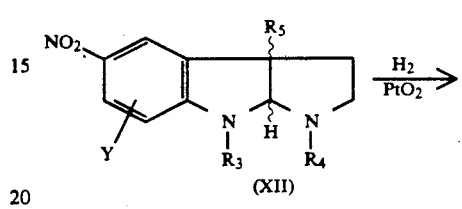

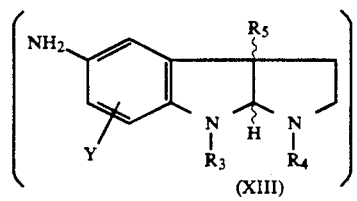

STEP J

Compound XIII is allowed to react with an isocyanate of the formula R₁NCO (R₁≠H) to afford a compound of Formula XIV. This reaction is typically conducted in a suitable solvent such as ethyl acetate at a temperature of −78° to 78° C.

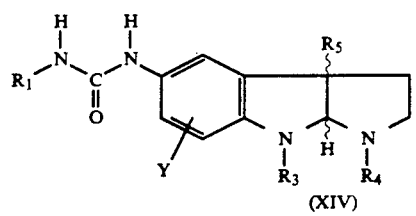

STEP K

Compound XIV is allowed to react with a strong base such as sec-BuLi to afford the corresponding anion and the latter is allowed to react with a halide compound of the formula R₂—Hal where R₂ is not hydrogen and Hal is chlorine or bromine, in a routine manner known to the art to afford a compound of Formula XV.

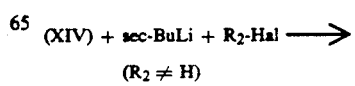

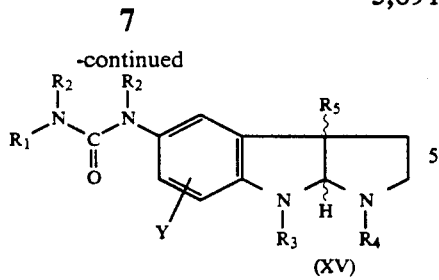

(XV)

STEP L

Compound XIII is allowed to react with a compound of Formula XVI or a compound of Formula XVII in the presence of a base such as triethylamine and/or 4-dimethylaminopyridine to afford a compound of Formula XVIII where X' O or S. Typically, this reaction is conducted in a suitable solvent such as ethyl acetate at a temperature of −78° to 78° C.

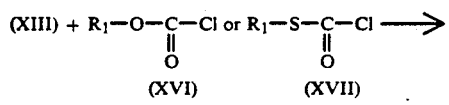

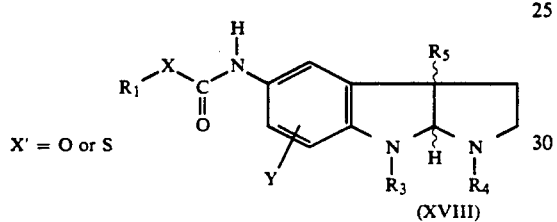

Where $R_1$ is tertiary butyl in the above reaction, di-tert-butyldicarbonate is used instead of compound XVI or XVII.

STEP M

Compound XVIII is allowed to react with a strong base such as sec-BuLi and the resultant anion is allowed to react with a halide compound of the formula $R_2$—Hal where $R_2$ is not hydrogen and Hal is chlorine or bromine, in a routine manner known to the art to afford a compound of Formula XIX.

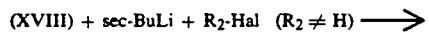

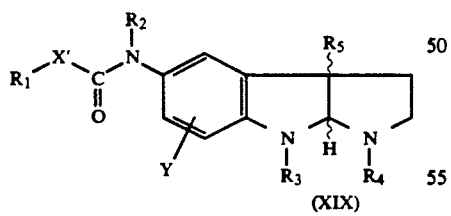

The same result can also be accomplished by allowing compound XVIII to react with lithium bis(trimethylsilyl)amide,

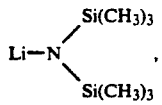

in a suitable solvent such as THF and thereafter allowing the resultant anion to react with a disulfate compound of the formula $R_2$—O—$SO_2$—O—$R_2$, or a mesylate of the formula $R_2$—O—$SO_2$—$CH_3$ or a chloride or bromide of the formula $R_2Cl$ or $R_2Br$ in a suitable solvent such as THF.

STEP N

As an alternative to STEP L above, one can introduce Cl, Br or $NO_2$ into the $C_7$ position of compound XVIII where Y is hydrogen and obtain compound XX where Y is Cl, Br or $NO_2$. To this end, compound XVIIIa is allowed to react with N-chlorosuccinimide, N-bromosuccinimide or $NO_2BF_4$ to afford compound XX where Y is Cl, Br or $NO_2$, respectively, according to a routine procedure known to the art.

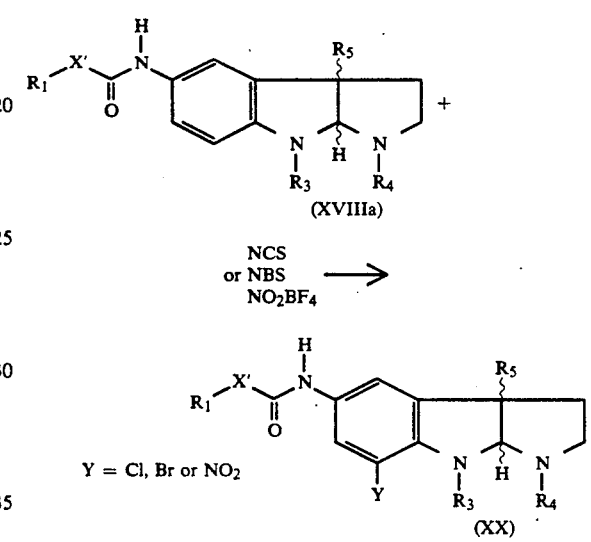

STEP O

Compound XIII is allowed to react with formic anhydride, generated in situ from formic acid and dicyclohexylcarbodiimide, to afford a compound of Formula XXI. Typically, this reaction is conducted in the presence of a suitable solvent such as tetrahydrofuran at a temperature of about 0°–50° C.

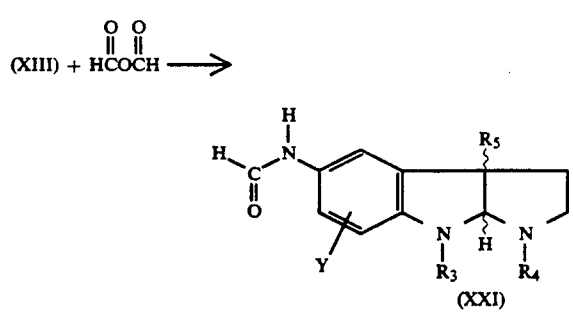

Alternatively, the above reaction can also be accomplished by using mixed formic-acetic anhydride in a routine manner known to the art.

STEP P

Compound XIII is allowed to react with an acid chloride of the formula $R_1$—CO—Cl in a routine manner known to the art to afford a compound of formula XXII.

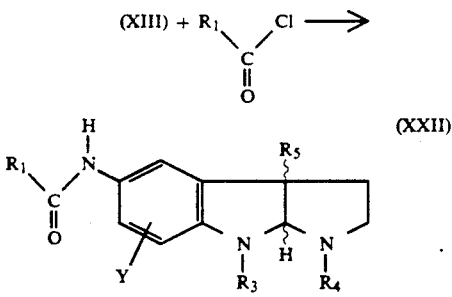

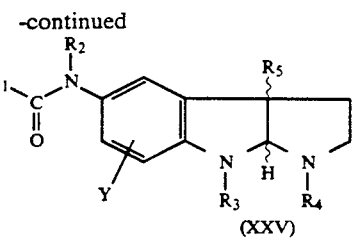

STEP Q

A compound of formula XIXa obtained from STEP M is converted to a compound of formula XXIII. This conversion is typically accomplished by heating compound XIXa at a temperature of about 150°–250°. Subsequently, compound XXIII is allowed to react with an isocyanate of the formula $R_1NCO$ in substantially the same manner as in STEP J to afford a compound of Formula XXIV.

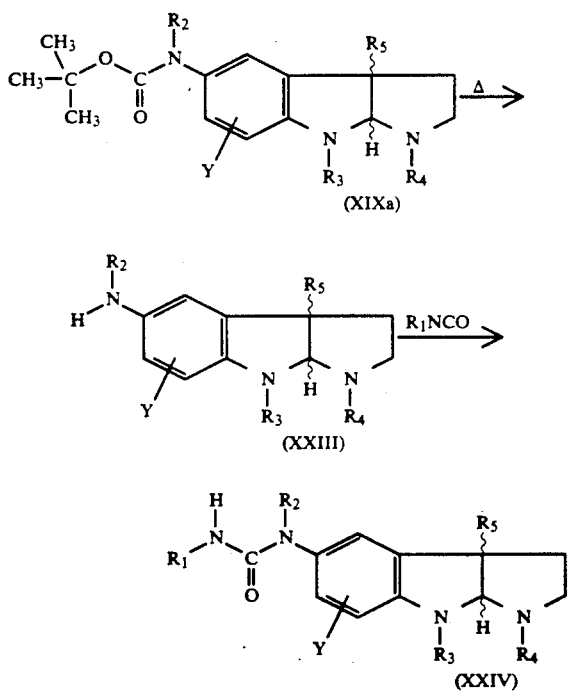

STEP R

Compound XXIII is allowed to react with an acid chloride of the formula $R_1$—CO—Cl in substantially the same manner as in STEP P to afford a compound of formula XXV.

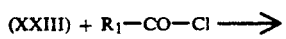

The compounds of Formula I of the present invention are useful for the treatment of various memory dysfunctions characterized by a decreased cholinergic function such as Alzheimer's disease.

This utility is manifested by the ability of these compounds to inhibit the enzyme acetylcholinesterase and thereby increase acetylcholine levels in the brain.

CHOLINESTERASE INHIBITION ASSAY

Cholinesterases are found throughout the body, both in the brain and in serum. However, only brain acetylcholinesterase (AChE) distribution is correlated with central cholinergic innervation. This same innervation is suggested to be weakened in Alzheimer patients. Therefore, specific inhibitors of brain AChE (as opposed to serum AChE) will give rise to fewer side effects and thus lower toxicity than physostigimine (a non-specific AChE inhibitor). We have determined in vitro inhibition of acetylcholinesterase activity in rat striatum.

IN VITRO INHIBITION OF ACETYLCHOLINESTERASE ACTIVITY IN RAT STRIATUM

Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in brain correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's dementia.

The method described below was used in this invention for assaying cholinesterase activity. This is a modification of the method of Ellman et al., Biochem. Pharmacol. 7, 98 (1961).

PROCEDURE

A. Reagents 1. 0.05M Phosphate Buffer, pH 7.2
   (a) 6.85 g $NaH_2PO_4 \cdot H_2O/100$ ml distilled $H_2O$
   (b) 13.40 g $Na_2HPO_4 \cdot 7H_2O/100$ ml distilled $H_2O$
   (c) add (a) to (b) until pH reaches 7.2
   (d) Dilute 1:10
2. Chromogen-Substrate Buffer
   (a) 9.9 mg 5,5-dithiobisnitrobenzoic acid (DTNB) (0.25 mM)
   (b) 99 mg s-acetylthiocholine chloride (5 mM)

(c) q.s. to 100 ml with 0.05M phosphate buffer, pH 7.2 (reagent 1)

3. For most assays, a 2 mM stock solution of the test drug is made up in a suitable solvent and serially diluted such that the final concentration in the preincubation step ranges from $10^{-3}$ to $10^{-6}$M. Different concentrations may be used depending on the potency of the drug.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2 using a Potter-Elvehjem homogenizer. A 50 microliter aliquot of the homogenate is added to 50 microliter vehicle of various concentrations of the test drug and preincubated for 10 minutes at room temperature.

C. Assay

1. For routine IC$_{50}$ determinations the Abbott Bichromatic Analyzer, ABA-100, is used to determine acetylcholinesterase activity.

| Instrument settings | |
|---|---|
| Filter: | 450-415 |
| Incubation temperature: | 30° C. |
| Decimal point: | 0000. |
| Analysis time: | 5 minutes |
| Carousel Revolution: | 3 |
| Reaction direction: | down endpoint |
| Syringe plate: | 1:101 dilution |

Following the 10 minute preincubation of the tissue (enzyme) with the inhibitor, the samples are mixed with the substrate chromogen buffer by the ABA-100. Using the indicated instrument settings the ABA-100 automatically reads the color reaction and prints out the results in enzyme units after 15 minutes.

2. The enzyme activity can also be measured with Gilford 250 spectrophotometer. This method is used for more accurate kinetic measurements.

| Instrument settings | |
|---|---|
| Lamp: | visible |
| Filter: | no filter |
| Wavelength: | 412 nm |
| Slit width: | 0.2 mm |
| Selection: | small aperture |
| Calibrated absorbance: | 1.0 unit full scale |
| Chart speed: | 0.5 cm/min |

Reagents are added to the reference and sample side of a split curvette as follows:

| Reference | Sample |
|---|---|
| 0.8 ml 0.05 M phosphate buffer | 0.8 ml 0.05 M phosphate buffer |
| 0.8 ml Chromogen-substrate buffer | 0.8 ml Chromogen-substrate buffer |
| | 10 microliter enzyme |

| Reference | Sample |
|---|---|
| | (tissue homogenate) |

The uninhibited activity of the enzyme (tissue homogenate) is first determined. Test drugs are made up in a suitable solvent and added in suitable dilutions to the buffer vehicle. The reaction rate is determined by the slope of the recorded absorbance change. The actual rate (moles/liter/min) can be calculated as described in the following formula:

$$\text{rate(moles/liter/min)} = \text{slope}/(1.36 \times 10^4)$$

Results of this assay for some of the compounds of this invention and physostigmine (reference compound) are presented in Table 1.

TABLE 1

| Compound | Inhibitory Concentration ($\mu$M) Brain AChE |
|---|---|
| 1,2,3,3a,8,8a-Hexahydro-5-(phenoxy-carbonylamino)-1,3a,8- trimethylpyrrolo-[2,3-b]indole oxalate | 14.0 |
| 5-(4-Chlorophenoxy-carbonylamino)-1,2,3,3a,8,8a-hexahydro-1,3a,8-trimethylpyrrolo[2,3-b]-indole oxalate | 1.1 |
| (Reference Compound) Physostigmine | 0.034 |

This utility is further demonstrated by the ability of these compounds to restore cholinergically deficient memory in the Dark Avoidance Assay described below.

DARK AVOIDANCE ASSAY

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

Results of this assay for some of the compounds of this invention and those for tacrine and pilocarpine (reference compounds) are presented in Table 2.

TABLE 2

| Compound | Dose (mg/kg of body weight, s.c) | % of Animals with Scopolamine Induced Memory Deficit Reversal |
| --- | --- | --- |
| 5-(t-Butoxy-carbonylamino)-1,2,3,3a,8,8a-hexahydro-1,3a,8-trimethylpyrrolo-[2,3-b]indole oxalate | 0.31<br>1.25<br>5.0 | 33<br>20<br>27 |
| 5-(Benzoxy-carbonylamino)-1,2,3,3a,8,8a-hexahydro-1,3a,8-trimethylpyrrolo-[2,3-b]indole | 0.3<br>1.0<br>3.0 | 28<br>21<br>21 |
| 1,2,3,3a,8,8a-Hexahydro-5-(phenoxycarbonylamino)-1,3a,8-trimethylpyrrolo-[2,3-b]indole oxalate | 0.16<br>0.31<br>5.0 | 53<br>40<br>21 |
| (Reference Compounds) | | |
| Tacrine | 0.63 | 13 |
| Pilocarpine | 5.0 | 13 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of the invention include those listed below as well as the 3aR-cis isomers thereof and mixtures of the 3aS-cis and 3aR-cis isomers including the racemic mixtures:

1,2,3,3a,8,8a-hexahydro-5-nitro-1,3a,8-trimethylpyrrolo[2,3-b]indole;

5,7-dinitro-1,2,3,3a,8,8a-hexahydro-1,3a,8-trimethylpyrrolo[2,3-b]indole;

1,2,3,3a,8,8a-hexahydro-5-(methylaminocarbonylamino)-1,3a,8-trimethylpyrrolo[2,3-b]indole;

1,2,3,3a,8,8a-hexahydro-5-(methoxycarbonylamino)-1,3a,8-trimethylpyrrolo[2,3-b]indole;

5-(ethoxycarbonylamino)-1,2,3,3a,8,8a-hexahydro-1,3a,8-trimethylpyrrolo[2,3-b]indole;

1,2,3,3a,8,8a-hexahydro-5-(trichloroethoxycar-
bonylamino)-1,3a,8-trimethylpyrrolo[2,3-b]indole;
5-(propoxycarbonylamino)-1,2,3,3a,8,8a-hexahydro-
1,3a,8-trimethylpyrrolo[2,3-b]indole;
5-(t-butoxycarbonylamino)-1,2,3,3a,8,8a-hexahydro-
1,3a,8-trimethylpyrrolo[2,3-b]indole;
1,2,3,3a,8,8a-hexahydro-5-(phenoxycarbonylamino)-
1,3a,8-trimethylpyrrolo[2,3-b]indole;
5-(4-methoxyphenoxycarbonylamino)-1,2,3,3a,8,8a-
hexahydro-1,3a,8-trimethylpyrrolo[2,3-b]indole;
5-(4-chlorophenoxycarbonylamino)-1,2,3,3a,8,8a-hex-
ahydro-1,3a,8-trimethylpyrrolo[2,3-b]indole;
5-(2,6-dimethylphenoxycarbonylamino)-1,2,3,3a,8,8a-
hexahydro-1,3a,8-trimethylpyrrolo[2,3-b]indole;
5-(benzoxycarbonylamino)-1,2,3,3a,8,8a-hexahydro-
1,3a,8-trimethylpyrrolo[2,3-b]indole;
5-(4-chlorobenzoylamino)-1,2,3,3a,8,8a-hexahydro-
1,3a,8-trimethylpyrrolo[2,3-b]indole;
5-(t-butoxycarbonyl-N-methylamino)-1,2,3,3a,8,8a-hex-
ahydro-1,3a,8-trimethylpyrrolo[2,3-b]indole;
5-(methylaminocarbonyl-N-methylamino)-1,2,3,3a,8-
,8a-hexahydro-1,3a,8-trimethylpyrrolo[2,3-b]indole;
1,2,3,3a,8,8a-hexahydro-5-(3-methylphenoxycarbonyl-
methylamino)-1,3a-8-trimethylpyrrolo[2,3-b]indole;
1,2,3,3a,8,8a-hexahydro-5-(2,4,6-trichlorophenoxycar-
bonylamino-6-trimethylsilyl-1,3a,8-trimethylpyr-
rolo[2,3-b]indole;
6-bromo-5-(4-fluorophenoxycarbonylamino)-1,2,3,3a,8-
,8a-hexahydro-1,3a,8-trimethylpyrrolo[2,3-b]indole;
1,2,3,3a,8,8a-hexahydro-5-(methoxycarbonylme-
thylamino)-1,3a,6,8-tetramethylpyrrolo[2,3-b]indole;
5-(4-dimethylaminophenoxycarbonylamino)-1,2,3,3a,8-
,8a-hexahydro-6-trimethylsilyl-1,3a,4,8-tetramethyl-
pyrrolo[2,3-b]indole;
5,7-bis-(t-butoxycarbonylamino)-1,2,3,3a,8,8a-hexahy-
dro-1,3a,8-trimethylpyrrolo[2,3-b]indole;
5-(4-trifluoromethylphenoxycarbonylamino)-1,3a-
dimethyl-8-ethyl-1,2,3,3a,8,8a-hexahydropyrrolo[2,3-
b]indole;
1,2,3,3a,8,8a-hexahydro-5-(3-thienyl)oxycar-
bonylamino-1,3a,8-trimethylpyrrolo[2,3-b]indole;
1,2,3,3a,8,8a-hexahydro-6-methoxy-5-(4-[pyridinylme-
thoxycarbonylamino)-1,3a,8-trimethylpyrrolo[2,3-
b]indole;
5-(butylthiocarbonylamino)-1,2,3,3a,8,8a-hexahydro-
1,3a,8-trimethylpyrrolo[2,3-b]indole;
1,2,3,3a,8,8a-hexahydro-5-(2-thiophenecarbonylamino)-
1,3a,8-trimethylpyrrolo[2,3-b]indole;
1,2,3,3a,8,8a-hexahydro-5-(2-methylpropionylamino)-
1,3a,8-trimethylpyrrolo[2,3-b]indole;
5-benzoylamino-1,2,3,3a,8,8a-hexahydro-1,3a,8-trime-
thylpyrrolo[2,3-b]indole;
5-ethyloxalylamino-1,2,3,3a,8,8a-hexahydro-1,3a,8-
trimethylpyrrolo[2,3-b]indole;
1,2,3,3a,8,8a-hexahydro-5-phenoxycarbonylamino-3a,8-
dimethyl-1-propargylpyrrolo[2,3-b]indole;
1,2,3,3a,8,8a-hexahydro-5-methoxycarbonylamino-1-
methoxycarbonyl-8-methylpyrrolo[2,3-b]indole; and
1-acetyl-1,2,3,3a,8,8a-hexahydro-8-methyl-5-phenox-
ycarbonylaminopyrrolo[2,3-b]indole;
The following examples are presented in order to
illustrate this invention.

EXAMPLE 1

1,2,3,3a,8,8a-Hexahydro-5-nitro-1,3a,8-trimethylpyr-
rolo[2,3-b]indole

To a stirred solution of 1,2,3,3a,8,8a-hexahydro-
1,3a,8-trimethylpyrrolo[2,3-b]indole (25.0 g) in acetoni-
trile (500 ml) at 0° C. was added nitronium tetrafluoro-
borate (18.65 g) dissolved in acetonitrile (500 ml) in a
dropwise manner over a period of 0.5 hour. The reac-
tion mixture was stirred at 0° C. for 1 hour and allowed
to warm to room temperature for an additional hour.
Ice and a dilute NaHCO$_3$ solution were added followed
by methylene chloride (800 ml). The layers were sepa-
rated and the aqueous layer was extracted with methy-
lene chloride (2×200 ml). The organic layers were
combined, dried (Na$_2$SO$_4$), and concentrated to give an
oil which was chromatographed twice on silica gel, first
eluting with 2.5% methanol/ethyl acetate and then with
2% methanol/methylene chloride to give 1,2,3,3a,8,8a-
hexahydro-5-nitro-1,3a,8-trimethylpyrrolo[2,3-b]indole
(7.7 g).

ANALYSIS: Calculated for C$_{13}$H$_{16}$N$_3$O$_2$: 63.14% C;
6.94% H; 16.99% N. Found: 62.86% C; 6.90% H;
16.82% N.

EXAMPLE 2

5,7-Dinitro-1,2,3,3a,8,8a-hexahydro-1,3a,8-trimethyl-
pyrrolo[2,3-b]indole

To a stirred solution of 1,2,3,3a,8,8a-hexahydro-
1,3a,8-trimethylpyrrolo[2,3-b]indole (3.7 g) in acetoni-
trile (100 ml) at 0° C. was added nitronium tetrafluoro-
borate (5.1 g) dissolved in acetonitrile (100 ml) in a
dropwise manner over a period of 0.5 hour. The reac-
tion mixture was stirred at 0° C. for 1 hour and allowed
to warm to room temperature for an additional hour.
Ice and a dilute NaHCO$_3$ solution were added followed
by methylene chloride (200 ml). The layers were sepa-
rated and the aqueous portion was extracted with meth-
ylene chloride (2×50 ml). The organic layers were
combined, dried (Na$_2$SO$_4$), and concentrated to give an
oil which was chromatographed on silica gel (eluting
with 2:1 hexane/acetone) to give 5,7-dinitro-1,2,3,3a,8-
,8a-hexahydro-1,3a,8-trimethylpyrrolo[2,3-b]indole (1.8
g).

ANALYSIS: Calculated for C$_{13}$H$_{16}$N$_4$O$_4$: 53.40% C;
5.53% H; 19.17% N. Found: 53.11% C; 5.44% H;
19.14% N.

EXAMPLE 3

1,2,3,3a,8,8a-Hexahydro-5-(methylaminocar-
bonylamino)-1,3a,8-trimethylpyrrolo[2,3-b]indole
mesotartrate hemihydrate 1,2,3,3a,8,8a-Hexahydro-5-nitro-1,3a,8-trimethylpyr-
rolo-[2,3-b]indole (2.6 g) was dissolved in ethyl acetate
(100 ml) and hydrogenated in a Parr apparatus at 45 psi
(pounds per square inch) using PtO$_2$ (250 mg) as a cata-
lyst. The reduction was complete within 3 hours. The
reduction mixture was filtered directly into a nitrogen
flushed flask. The mixture was cooled to 0° C., a solu-
tion of methylisocyanate (0.6 g) in ethyl acetate (100 ml)
was added over a period of 2 hours and the mixture was
stirred for an additional 2 hours at room temperature.
The mixture was washed with water (2×100 ml), dried
(Na$_2$SO$_4$), concentrated and purified by flash chroma-
tography (eluting with 15% MeOH/EtOAc). The pure
fractions were concentrated to give 1,2,3,3a,8,8a-hex-
ahydro-5-(methylaminocarbonylamino)-1,3a,8-trime-
thylpyrrolo[2,3-b]-indole (1.05 g). The meso-tartarate
was prepared by dissolving the free base in ether (200
ml) and MeOH (10 ml) and adding a solution of meso-
tartaric acid in ether.

ANALYSIS: Calculated for $C_{15}H_{22}N_4O_7 \cdot C_4H_6O_6 \cdot \frac{1}{2}H_2O$: 52.64% C; 6.75% H; 12.92% N. Found: 52.66% C; 6.47% H; 12.90% N.

EXAMPLE 4

1,2,3,3a,8,8a-Hexahydro-5-(methoxycarbonylamino)-1,3a,8-trimethylpyrrolo[2,3-b]indole oxalate 1,2,3,3a,8,8a-Hexahydro-5-nitro-1,3a,8-trimethylpyrrolo[2,3-b]indole (1.0 g) was dissolved in ethyl acetate (100 ml) and hydrogenated in a Parr apparatus at 45 psi using $PtO_2$ (100 mg) as a catalyst. The reduction was complete within 2 hours. The reduction mixture was filtered directly into a nitrogen flushed flask. 4-Dimethylaminopyridine (50 mg) was added, the mixture was cooled to 0° C. and a solution of dimethylpyrocarbonate (0.54 g) in ethyl acetate (50 ml) was added over a period of 1 hour. The mixture was concentrated and purified by flash chromatography on silica gel (eluting with 15% MeOH/EtOAc). The pure fractions were concentrated to give 1,2,3,3a,8,8a-hexahydro-5-(methyloxycarbonylamino)-1,3a,8-trimethylpyrrolo[2,3-b]indole (0.4 g) and the oxalate salt was prepared by dissolving the free base in ether and a minimal amount of methanol and adding a solution of oxalic acid in ether.

ANALYSIS: Calculated for $C_{15}H_{21}N_3O_2 \cdot C_2H_2O_4$: 55.87% C; 6.08% H; 11.50% N. Found: 55.66% C; 6.28% H; 11.42% N.

EXAMPLE 5

5-(Ethoxycarbonylamino)-1,2,3,3a,8,8a-hexahydro-1,3a,8-trimethylpyrrolo[2,3-b]indole oxalate 1,2,3,3a,8,8a-Hexahydro-5-nitro-1,3a,8-trimethylpyrrolo[2,3-b]indole (1.0 g) was dissolved in ethyl acetate (100 ml) and hydrogenated in a Parr apparatus at 45 psi using $PtO_2$ (100 mg) as a catalyst. The reduction was complete within 2 hours. The reduction mixture was filtered directly into a nitrogen flushed flask. 4-Dimethylaminopyridine (50 mg) and triethylamine (0.14 g) were added, the mixture was cooled to 0° C. and a solution of ethylchloroformate (0.44 g) in ethyl acetate (70 ml) was added over a period of 1.5 hours. The mixture was washed with water (2×100 ml), dried ($Na_2SO_4$), concentrated and purified by flash chromatography on silica gel (eluting with 15% MeOH/EtOAc). The pure fractions were concentrated to give 5-ethoxycarbonylamino-1,2,3,3a,8,8a-hexahydro-1,3a,8-trimethylpyrrolo[2,3-b]indole (0.6 g). The oxalate salt was prepared by dissolving the free base in ether (200 ml) and a minimum amount of MeOH (20 ml) and adding a solution of oxalic acid in ether.

ANALYSIS: Calculated for $C_{16}H_{23}N_3O_2 \cdot C_2H_2O_4$: 56.97% C; 6.65% H; 11.07% N. Found: 56.93% C; 6.58% H; 11.03% N.

EXAMPLE 6

1,2,3,3a,8,8a-Hexahydro-5-(trichloroethoxycarbonylamino)-1,3a,8-trimethylpyrrolo[2,3-b]indole 1,2,3,3a,8,8a-Hexahydro-5-nitro-1,3a,8-trimethylpyrrolo[2,3-b]indole (2.2 g) was dissolved in ethyl acetate (100 ml) and hydrogenated in a Parr apparatus at 45 psi using $PtO_2$ (160 mg) as a catalyst. The reduction was complete within 3 hours. The reduction mixture was filtered directly into a nitrogen flushed flask. 4-Dimethylaminopyridine (0.109 g) and triethylamine (0.89 g) were added, the mixture was cooled to 0° C. and a solution of trichloroethylchloroformate (1.88 g) in ethyl acetate (100 ml) was added over a period of 2 hours. The mixture was washed with water (2×100 ml), dried ($Na_2SO_4$), concentrated and purified by flash chromatography on silica gel (eluting with 15% MeOH/EtOAc). The pure fractions were concentrated to give 1,2,3,3a,8,8a-hexahydro-5-(trichloroethoxycarbonyamino)-1,3a,8-trimethylpyrrolo[2,3-b]indole (0.8 g).

ANALYSIS: Calculated for $C_{16}H_{20}Cl_3N_3O_2$: 48.90% C; 5.14% H; 10.70% N. Found: 49.08% C; 5.06% H; 10.77% N.

EXAMPLE 7

5-(Propoxycarbonylamino)-cis-1,2,3,3a,8,8a-hexahydro-1,3a,8-trimethylpyrrolo[2,3-b]indole oxalate A 500 mL Parr bottle was charged with 0.370 g of platinum oxide catalyst and 1.51 g of 5-nitro-1,2,3,3a,8,8a-hexahydro-1,3a,8-trimethylpyrrolo[2,3-b]indole in 250 mL of HPLC grade ethyl acetate. The bottle was placed on a Parr apparatus, purged with hydrogen gas, and shaken at room temperature at the average pressure of 55 psi hydrogen. After 24 hours, the solution was filtered directly into a nitrogen purged flask to remove the catalyst. To the mechanically stirred solution were added 0.66 g of triethylamine, 0.19 g of 4-dimethylaminopyridine, and an additional 50 mL of HPLC grade ethyl acetate. The solution was chilled to 0° C. using an ice/water bath and treated dropwise with a solution of 0.72 g of propylchloroformate in 150 mL of HPLC grade ethyl acetate. The reaction was monitored via thin layer analysis on silica gel. The reaction was quenched with 150 mL of water and the resulting mixture was stirred vigorously for 5 minutes and transferred to a separatory funnel. The aqueous phase was removed and discarded. The dried ($Na_2SO_4$) organic phase was filtered and concentrated to a dark oil in vacuo. The oil was shown to be a multi-component mixture which was separated via preparative HPLC on silica gel. The pure oil was dissolved in 150 mL of anhydrous diethyl ether and treated dropwise with agitation with a slight excess of anhydrous oxalic acid in anhydrous diethyl ether. The resulting solids were collected by filtration under inert atmosphere and washed on the funnel with small portions of anhydrous diethyl ether to give 1.07 of the oxalate product as a powdery solid, m.p. 153°–155° C. (dec.).

ANALYSIS: Calculated for $C_{17}H_{25}N_3O_2 \cdot C_2H_2O_4$: 58.00% C; 6.92% H; 10.68% N. Found: 58.66% C; 6.88% H; 10.95% N.

EXAMPLE 8

5-(t-Butoxycarbonylamino)-1,2,3,3a,8,8a-hexahydro-1,3a,8-trimethylpyrrolo[2,3-b]indole oxalate 1,2,3,3a,8,8a-Hexahydro-5-nitro-1,3a,8-trimethylpyrrolo[2,3-b]indole (1.9 g) was dissolved in ethyl acetate and hydrogenated in a Parr apparatus at 45 psi using $PtO_2$ as a catalyst. The reduction was complete within 2 hours. The reduction mixture was filtered directly into a nitrogen flushed flask containing di-tert-butyldicarbonate (1.8 g). 4-Dimethylaminopyridine (85 mg) was added and the reaction mixture was stirred for 3 hours at room temperature. Water (50 ml) was added and the layers were separated. The ethyl acetate solution was dried over $Na_2SO_4$, filtered and concentrated to give an oil which was purified by chromatography on silica gel (eluting with 15% MeOH/EtOAc). The pure fractions were collected and concentrated to give the free base (800 mg), which was transformed to its oxalate salt by dissolving in ether (100 ml) and adding a solution of oxalic acid (300 mg) in ether (25 ml).

ANALYSIS: Calculated for $C_{18}H_{27}N_3O_6 \cdot C_2H_4O_4$: 58.95% C; 7.17% H; 10.31% N. Found: 58.81% C; 7.10% H; 10.21% N.

EXAMPLE 9

1,2,3,3a,8,8a-Hexahydro-5-(phenoxycarbonylamino)-1,3a,8-trimethylpyrrolo[2,3-b]indole oxalate 1,2,3,3a,8,8a-Hexahydro-5-nitro-1,3a,8-trimethylpyrrolo[2,3-b]indole (2.2 g) was dissolved in ethyl acetate (100 ml) and hydrogenated in a Parr apparatus at 45 psi using $PtO_2$ (220 mg) as a catalyst. The reduction was complete within 2 hours. The reduction mixture was filtered directly into a nitrogen flushed flask. 4-Dimethylaminopyridine (0.100 g) and triethylamine (0.9 g) were added, the mixture was cooled to 0° C. and a solution of phenylchloroformate (1.4 g) in ethyl acetate (100 ml) was added over a period of 1.5 hours. The mixture was washed with water (2×100 ml), dried ($Na_2SO_4$), concentrated and purified by flash chromatography (eluting with 15% MeOH/EtOAc). The pure fractions were concentrated to give 1,2,3,3a,8,8a-hexahydro-5-(phenoxycarbonylamino)-1,3a,8-trimethylpyrrolo[2,3-b]-indole (0.66 g), which was transformed to the oxalate salt by dissolving in ether (200 ml) and methanol (20 ml) and adding a solution of oxalic acid (0.16 g) in ether.

ANALYSIS: Calculated for $C_{22}H_{23}N_3O_2 \cdot C_2H_2O_4$: 61.82% C; 5.90% H; 9.83% N. Found: 61.75% C; 5.93% H; 10.04% N.

EXAMPLE 10

5-(4-Methoxyphenoxycarbonylamino)-1,2,3,3a,8,8a-hexahydro-1,3a,8-trimethylpyrrolo[2,3-b]indole oxalate 1,2,3,3a,8,8a-Hexahydro-5-nitro-1,3a,8-trimethylpyrrolo[2,3-b]indole (3.8 g) was dissolved in ethyl acetate (200 ml) and hydrogenated on a Parr apparatus at 45 psi using $PtO_2$ (380 mg) as a catalyst. The reduction mixture was filtered directly into a nitrogen flushed flask. 4-Dimethylaminopyridine (183 mg) and triethylamine (3.0 g) were added and the mixture cooled to 0° C. before the addition of a solution of 4-methoxyphenyl chloroformate (2.8 g) in ethyl acetate (60 ml) over a period of 1.5 hours. The mixture was washed with water (2×100 ml), dried ($Na_2SO_4$), concentrated and purified by flash chromatography. The pure fractions were concentrated to give 5-(4-methoxyphenoxycarbonylamino)-1,2,3,3a,8,8a-hexahydro-1,3a,8-trimethylpyrrolo[2,3-b]indole (1.0 g). The oxalate salt prepared by dissolving the free base in $Et_2O$ (200 ml) and adding oxalic acid (240 mg) $Et_2O$ (40 ml).

ANALYSIS: Calculated for $C_{21}H_{25}N_3O_3 \cdot C_2H_2O_4$: 60.39% C; 5.95% H; 9.18% N. Found: 59.97% C; 5.88% H; 9.35% N.

EXAMPLE 11

5-(4-Chlorophenoxycarbonylamino)-1,2,3,3a,8,8a-hexahydro-1,3a,8-trimethylpyrrolo[2,3-b]indole oxalate A 500 mL Parr bottle was charged with 0.450 g of platinum oxide catalyst and 7.23 g of 5-nitro-1,2,3,3a,8,8a-hexahydro-1,3a,8-trimethylpyrrolo[2,3-b]indole in 250 mL of HPLC grade ethyl acetate. The bottle was placed on a Parr apparatus, purged with hydrogen gas, and shaken at room temperature at the average pressure of 55 psi hydrogen. After 24 hours, the solution was filtered directly into a nitrogen purged flask to remove the hydrogenation catalyst. To the mechanically stirred solution were added 2.94 g of triethylamine, 0.37 g of 4-dimethylaminopyridine, and an additional 40 mL of HPLC grade ethyl acetate. The solution was chilled to 0° C. using an ice/water bath and treated dropwise with a solution of 5.54 g of 4-chlorophenyl chloroformate in 250 mL of HPLC grade ethyl acetate. The reaction was monitored via thin layer analysis on silica gel. The reaction was quenched with 150 mL of water and the resulting mixture was stirred vigorously for 10 minutes and transferred to a separatory funnel. The aqueous phase was removed and discarded. The dried ($Na_2SO_4$) organic phase was filtered and concentrated to a dark foam in vacuo. The foam was shown to be a multi-component mixture which was separated via preparative HPLC on silica gel to give 1.51 g of a pure oil. The pure oil was dissolved in 250 mL of anhydrous diethyl ether and filtered, and the filtrate was treated dropwise with agitation with a slight excess of anhydrous oxalic acid in anhydrous diethyl ether. The resulting precipitate was collected by filtration under an inert atmosphere and washed on the funnel with small portions of anhydrous diethyl ether to give a powdery solid, mp. 110° C. (dec.).

ANALYSIS: Calculated for $C_{20}H_{22}ClN_3O_2 \cdot C_2H_2O_4$: 57.21% C; 5.24% H; 9.10% N. Found: 57.23% C; 5.35% H; 9.36% N.

EXAMPLE 12

5-(2,6-Dimethylphenoxycarbonylamino)-1,2,3,3a,8,8a-hexahydro-1,3a,8-trimethylpyrrolo[2,3-b]indole 1,2,3,3a,8,8a-Hexahydro-5-nitro-1,3a,8-trimethylpyrrolo[2,3-b]indole (3.0 g) was dissolved in ethyl acetate (200 ml) and hydrogenated on a Parr apparatus at 45 psi using $PtO_2$ (300 mg) as a catalyst. The reduction mixture was filtered directly into a nitrogen flushed flask. 4-Dimethylaminopyridine (145 mg) and triethylamine (2.4 g) were added and the mixture cooled to 0° C. A solution of 2,6-dimethylphenylchloroformate (2.2 g) in ethyl acetate (60 ml) was added over a period of 1.5 hours. The mixture was washed with water (2×100 ml), dried ($Na_2SO_4$), concentrated and purified by flash chromatography on silica gel. The pure fractions were concentrated to give 5-(2,6-dimethylphenoxycarbonylamino-1,2,3,3a,8,8a-hexahydro-1,3a,8-trimethylpyrrolo[2,3-b]indole (2.04 g).

ANALYSIS: Calculated for $C_{22}H_{27}N_3O_2$: 72.30%C; 7.45% H; 11.50% N. Found: 71.86% C; 7.43% H; 11.56% N.

EXAMPLE 13

5-(Benzoxycarbonylamino)-1,2,3,3a,8,8a-hexahydro-1,3a,8-trimethylpyrrolo[2,3-b]indole 1,2,3,3a,8,8a-Hexahydro-5-nitro-1,3a,8-trimethylpyrrolo[2,3-b]indole (2.2 g) was dissolved in ethyl acetate (100 ml) and hydrogenated in a Parr apparatus at 45 psi using $PtO_2$ (220 mg) as a catalyst. The reduction was complete within 2 hours. The reduction mixture was filtered directly into a nitrogen flushed flask. 4-Dimethylaminopyridine (0.100 g) and triethylamine (0.9 g) were added, the mixture was cooled to 0° C. and a solution of benzylchloroformate (1.5 g) in ethyl acetate (100 ml) was added over a period of 1.5 hours. The mixture was washed with water (2×100 ml), dried ($Na_2SO_4$), concentrated and purified by flash chromatography on silica gel (eluting with 15% MeOH- /EtOAc). The pure fractions were concentrated to give 5-(benzoxycarbonylamino)-1,2,3,3a,8,8a-hexahydro-1,3a,8-trimethylpyrrolo-[2,3-b]indole (1.2 g).

ANALYSIS: Calculated for $C_{21}H_{25}N_3O_2$: 71.75% C; 7.18% H; 11.96% N. Found: 71.70% C; 7.16% H; 11.98% N.

EXAMPLE 14

5-(4-Chlorobenzoylamino)-1,2,3,3a,8,8a-hexahydro-1,3a,8-trimethylpyrrolo[2,3-b]indole 1,2,3,3a,8,8a-Hexahydro-5-nitro-1,3a,8-trimethylpyrrolo[2,3-b]indole (6.8 g) was dissolved in ethyl acetate (300 ml) and hydrogenated on a Parr apparatus at 45 psi using $PtO_2$ (680 mg) as a catalyst. The reduction mixture was filtered directly into a nitrogen-flushed flask, 4-dimethylaminopyridine (330 mg) and triethylamine (5.5 grams) were added and the mixture was cooled to 0° C. A solution of 4-chlorobenzoyl chloride (4.4 g) in ethyl acetate (100 ml) was added over a period of 1.5 hours. The mixture was washed with water (2×150 ml), dried ($Na_2SO_4$), concentrated and purified by flash chromatography. The pure fractions were concentrated to give 5-(4-chlorobenzoylamino)-1,2,3,3a,8,8a-hexahydro-1,3a,8-trimethylpyrrolo-[2,3-b]indole (2.5 g) as a solid.

ANALYSIS: Calculated for $C_{20}H_{22}ClN_3O$: 67.50% C; 6.23% H; 11.81% N. Found: 67.20% C; 6.30% H; 11.91% N.

EXAMPLE 15

5-(t-Butoxycarbonyl-N-methylamino)-1,2,3,3a,8,8a-hexahydro-1,3a,8-trimethylpyrrolo[2,3-b]indole 5-(t-Butyloxycarbonylamino)-1,2,3,3a,8,8a-hexahydro-1,3a,8-trimethylpyrrolo[2,3-b]indole (1.7 g) was dissolved in dry THF (15 ml) under nitrogen and cooled to −78° C. in a dry ice/acetone bath. A 1M solution of lithium bis(trimethylsilyl)amide (7.2 ml) in THF was added via a syringe. The solution was stirred at −78° C. for 15 minutes, warmed to room temperature and again cooled to −78° C. before the addition of dimethylsulfate (0.74 g) in THF (5 ml) via syringe. The mixture was stirred for 1 hour and allowed to warm to ambient temperature and water was added in order to quench the reaction. Ethyl acetate (100 ml) was added and the mixture was washed with brine (20 ml), dried ($Na_2SO_4$), concentrated and purified by flash chromatography (eluting with 15% MeOH/EtOAc). The pure fractions were concentrated to give 5-(t-butoxycarbonyl-N-methylamino)-1,2,3,3a,8,8a-hexahydro-1,3a,8-trimethylpyrrolo[2,3-b]indole (0.42 g).

EXAMPLE 16

5-(N-Methylaminocarbonyl-N-methylamino)-1,2,3,3a,8,8a-hexahydro-1,3a,8-trimethylpyrrolo[2,3-b]indole 5-(t-Butoxycarbonyl-N-methylamino)-1,2,3,3a,8,8a-hexahydro-1,3a,8-trimethylpyrrolo[2,3-b]indole (100 mg) was heated under nitrogen without solvent to 200°–210° C. in an oil bath. After 1 hour, TLC (thin layer chromatography) indicated a conversion to a new compound. The flask was allowed to cool to ambient temperature and dichloromethane (5 ml) was added followed by the slow addition of a solution of methyl isocyanate (18 mg) in dichloromethane (3 ml) over a period of 45 minutes. The mixture was washed with water (2 ml), dried ($Na_2SO_4$), concentrated and purified by flash chromatography (eluting with 15% MeOH/EtOAc). The pure fractions were concentrated to give 5-(methylaminocarbonyl-N-methylamino)-1,2,3,3a,8-,8a-hexahydro-1,3a,8-trimethylpyrrolo[2,3-b]indole (0.05 g).

We claim:

1. A method of preparing a compound of the formula,

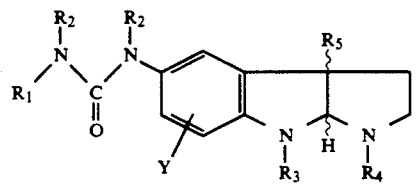

where
- Y is hydrogen, fluorine, chlorine, bromine, nitro, loweralkyl, loweralkoxy or triloweralkylsilyl;
- $R_1$ is loweralkyl, halogen-substituted loweralkyl, aryl, arylloweralkyl, cycloalkyl having from 3 to 7 carbon atoms in the ring, heteroaryl or heteroaryl-loweralkyl;
- $R_2$ is loweralkyl or arylloweralkyl;
- $R_3$ is loweralkyl or arylloweralkyl;
- $R_4$ is hydrogen, loweralkyl, loweralkenyl, loweralkynyl, arylloweralkyl, formyl, loweralkylcarbonyl, arylloweralkylcarbonyl or loweralkoxycarbonyl;
- $R_5$ is hydrogen or loweralkyl;

wherein the term heteroaryl signifies a group depicted by the formula

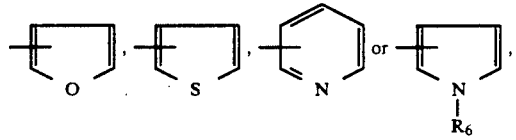

where $R_6$ is hydrogen or loweralkyl;

which comprises reacting a compound of the formula,

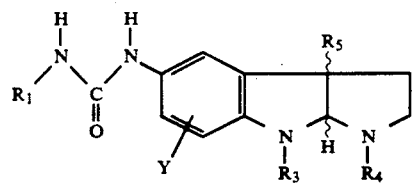

with a strong base and allowing the resultant anion to react with a compound of the formula $R_2$—Cl or $R_2$—Br to afford said compound.

2. A method of preparing a compound of the formula,

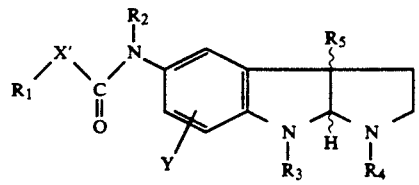

where $R_1$ is loweralkyl, halogen-substituted loweralkyl, aryl, arylloweralkyl, cycloalkyl having from 3 to 7 carbon atoms in the ring, heteroaryl or heteroarylloweralkyl;

$R_2$ is loweralkyl or arylloweralkyl;

$R_3$ is loweralkyl or arylloweralkyl;

$R_4$ is hydrogen, loweralkyl, loweralkenyl, loweralkynyl, arylloweralkyl, formyl, loweralkylcarbonyl, arylloweralkylcarbonyl or loweralkoxycarbonyl;

$R_5$ is hydrogen or loweralkyl;

X' is oxygen or sulfur; and

Y is hydrogen, fluorine, chlorine, bromine, nitro, loweralkyl, loweralkoxy or triloweralkylsilyl;

wherein the term heteroaryl signifies a group depicted by the formula where $R_6$ is hydrogen or loweralkyl;

which comprises reacting a compound of the formula, with Li—N(Si(CH$_3$)$_3$)$_2$ and thereafter reacting the resultant anion with a disulfate compound of the formula $R_2$—O—SO$_2$—O—$R_2$ or a mesylate of the formula $R_2$O—SO$_2$—CH$_3$ or a chloride or bromide of the formula $R_2$Cl or $R_2$Br to afford said compound.

3. A method of preparing a compound of the formula, where $R_1$ is loweralkyl, halogen-substituted loweralkyl, aryl, arylloweralkyl, cycloalkyl having from 3 to 7 carbon atoms in the ring, heteroaryl or heteroarylloweralkyl;

$R_2$ is loweralkyl or arylloweralkyl;

$R_3$ is loweralkyl or arylloweralkyl;

$R_4$ is hydrogen, loweralkyl, loweralkenyl, loweralkynyl, arylloweralkyl, formyl, loweralkylcarbonyl, arylloweralkylcarbonyl or loweralkoxycarbonyl;

$R_5$ is hydrogen or loweralkyl; and

Y is hydrogen, fluorine, chlorine, bromine, nitro, loweralkyl, loweralkoxy or triloweralkylsilyl;

wherein the term heteroaryl signifies a group depicted by the formula where $R_6$ is hydrogen or loweralkyl;

which comprises converting a compound of the formula, to an amine compound of the formula, by heating at a temperature of about 150°–250° C. in the absence of base and thereafter allowing the latter compound to react with an isocyanate of the formula $R_1$NCO to afford said compound.

4. The method of claim 1 wherein the strong base is sec-BuLi.

* * * * *